(12) United States Patent
Lindenthaler

(10) Patent No.: US 9,731,131 B2
(45) Date of Patent: *Aug. 15, 2017

(54) PACEMAKER FOR UNILATERAL VOCAL CORD AUTOPARALYSIS

(71) Applicant: MED-EL Elektromedizinische Geraete GmbH, Innsbruck (AT)

(72) Inventor: Werner Lindenthaler, Oberperfuss (AT)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 0 days.

This patent is subject to a terminal disclaimer.

(21) Appl. No.: 15/156,885

(22) Filed: May 17, 2016

(65) Prior Publication Data

US 2016/0256684 A1 Sep. 8, 2016

Related U.S. Application Data

(63) Continuation-in-part of application No. 14/703,486, filed on May 4, 2015, now Pat. No. 9,345,885, which
(Continued)

(51) Int. Cl.
*A61N 1/36* (2006.01)
*A61N 1/05* (2006.01)
(Continued)

(52) U.S. Cl.
CPC .......... *A61N 1/3606* (2013.01); *A61B 5/0492* (2013.01); *A61B 5/04886* (2013.01); *A61B 5/686* (2013.01); *A61H 23/00* (2013.01);

*A61H 23/02* (2013.01); *A61N 1/0556* (2013.01); *A61N 1/36003* (2013.01); *A61N 1/36053* (2013.01);
(Continued)

(58) Field of Classification Search
None
See application file for complete search history.

(56) References Cited

U.S. PATENT DOCUMENTS

| 4,198,542 A | 4/1980 | Ducommun |
| 5,016,647 A | 5/1991 | Sanders |

(Continued)

FOREIGN PATENT DOCUMENTS

| WO | 02081026 A2 | 10/2002 |
| WO | 2010033594 A2 | 3/2010 |
| WO | 2011119812 A2 | 9/2011 |

OTHER PUBLICATIONS

Ikari et al., "Glottic closure reflex: control mechanisms," Ann Otol Rhinol Laryngol, 89, May-Jun. 1980, pp. 220-224.
(Continued)

*Primary Examiner* — Kennedy Schaetzle
(74) *Attorney, Agent, or Firm* — Sunstein Kann Murphy & Timbers LLP

(57) ABSTRACT

A method for treating a human subject having unilateral vocal cord paralysis includes sensing electrical activity of a dysfunctional muscle of the subject, generating at least one stimulation parameter, using a processor, based on the sensed electrical activity, and stimulating the dysfunctional muscle, using a stimulating electrode, based on the at least one stimulation parameter. A stimulation system is also provided.

18 Claims, 6 Drawing Sheets

Related U.S. Application Data is a continuation-in-part of application No. 13/708,129, filed on Dec. 7, 2012, now Pat. No. 9,026,204.

(60) Provisional application No. 61/567,664, filed on Dec. 7, 2011, provisional application No. 61/567,666, filed on Dec. 7, 2011.

(51) Int. Cl.

| | | |
|---|---|---|
| *A61H 23/00* | (2006.01) | |
| *A61B 5/0492* | (2006.01) | |
| *A61H 23/02* | (2006.01) | |
| *A61B 5/00* | (2006.01) | |
| *A61B 5/0488* | (2006.01) | |

(52) U.S. Cl.
CPC ..... *A61N 1/36139* (2013.01); *A61N 1/36171* (2013.01); *A61N 1/3611* (2013.01); *A61N 1/36157* (2013.01); *A61N 1/36175* (2013.01)

(56) References Cited

U.S. PATENT DOCUMENTS

| | | |
|---|---|---|
| 5,111,814 A | 5/1992 | Goldfarb |
| 5,540,732 A | 7/1996 | Testerman |
| 5,897,579 A | 4/1999 | Sanders |
| 6,978,787 B1 | 12/2005 | Broniatowski |
| 7,258,660 B1 | 8/2007 | Sarfati |
| 7,801,603 B2 | 9/2010 | Westlund et al. |
| 7,805,195 B2 | 9/2010 | Zealear |
| 8,065,014 B2 | 11/2011 | Zealear |
| 8,219,188 B2 | 7/2012 | Craig |
| 8,457,747 B2 | 6/2013 | Terry, Jr. |
| 8,731,683 B2 | 5/2014 | Lindenthaler |
| 9,026,204 B2 | 5/2015 | Lindenthaler |
| 9,050,462 B2 | 6/2015 | Lindenthaler |
| 9,345,885 B2 * | 5/2016 | Lindenthaler ........ A61B 5/0492 |
| 2002/0156507 A1 | 10/2002 | Lindenthaler |
| 2003/0093128 A1 | 5/2003 | Freed et al. |
| 2006/0282127 A1 | 12/2006 | Zealear |
| 2007/0027482 A1 | 2/2007 | Parnis et al. |
| 2007/0123950 A1 | 5/2007 | Ludlow et al. |
| 2008/0091247 A1 | 4/2008 | Muller et al. |
| 2008/0208280 A1 | 8/2008 | Lindenthaler et al. |
| 2009/0054980 A1 | 2/2009 | Ludlow et al. |
| 2009/0177127 A1 | 7/2009 | Sherman et al. |
| 2009/0187124 A1 | 7/2009 | Ludlow et al. |
| 2009/0270943 A1 | 10/2009 | Maschino |
| 2010/0125310 A1 | 5/2010 | Wilson et al. |
| 2010/0145178 A1 | 6/2010 | Kartush |
| 2011/0093032 A1 | 4/2011 | Boggs, II et al. |
| 2011/0125212 A1 | 5/2011 | Tyler |
| 2011/0190596 A1 | 8/2011 | Hacker et al. |
| 2013/0053926 A1 | 2/2013 | Hincapie Ordonez et al. |
| 2013/0131551 A1 | 5/2013 | Raghunathan et al. |
| 2013/0245486 A1 | 9/2013 | Simon et al. |

OTHER PUBLICATIONS

International Searching Authority—International Search Report—International Application No. PCT/US2012/068542, dated Feb. 15, 2013, together with the Written Opinion of the International Searching Authority, 12 pages.

* cited by examiner

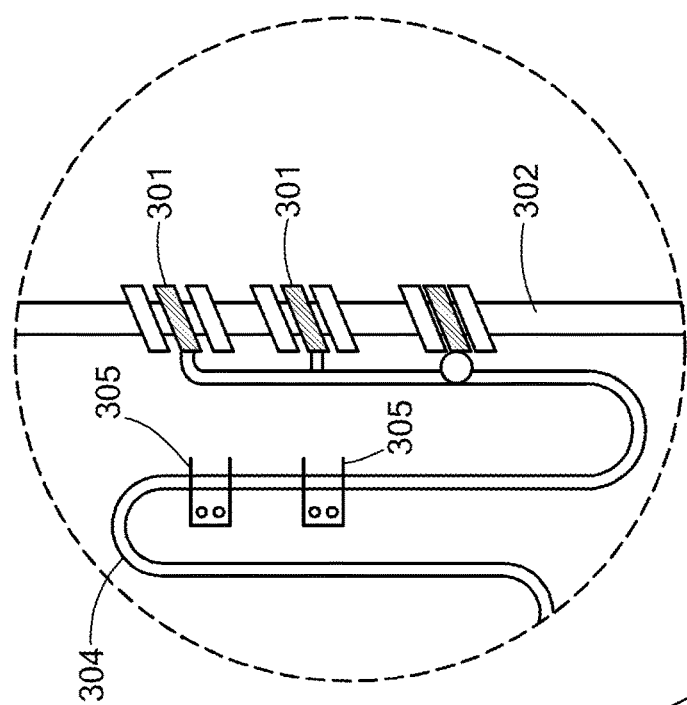
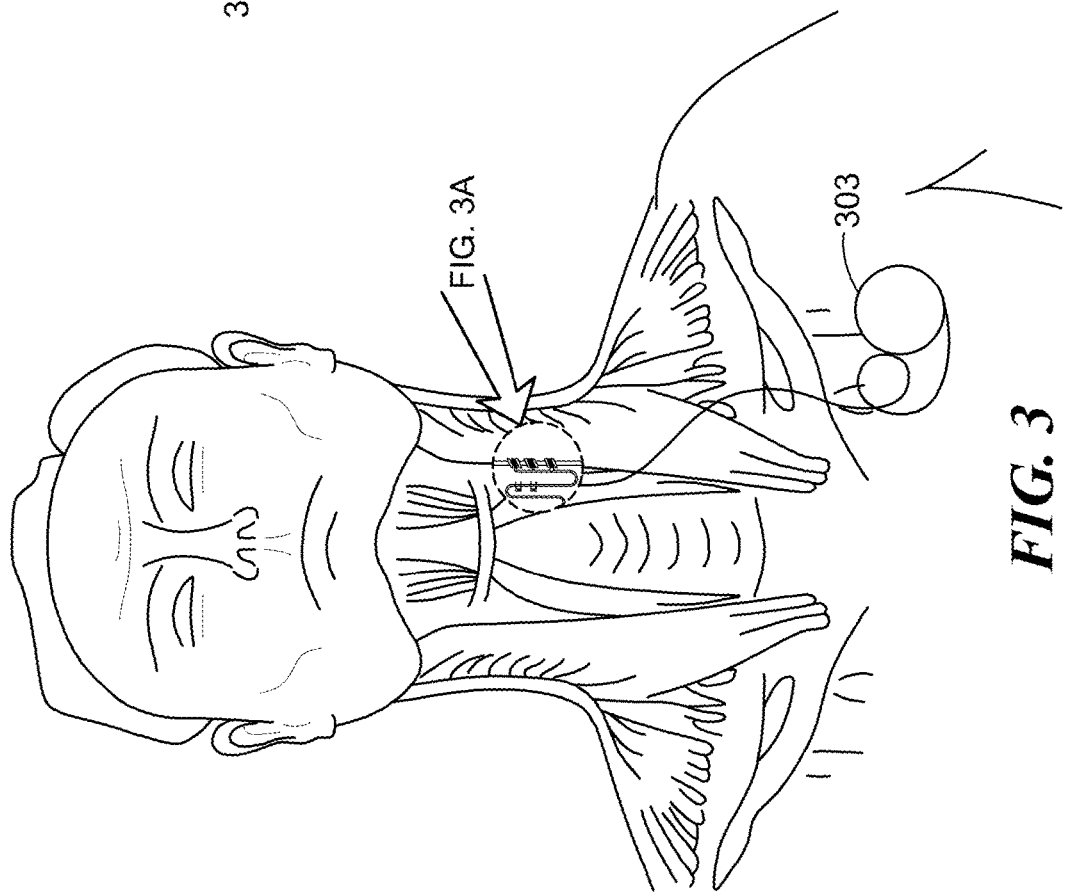
*FIG. 3A*
*FIG. 3*

PACEMAKER FOR UNILATERAL VOCAL CORD AUTOPARALYSIS

CROSS REFERENCE TO RELATED APPLICATIONS

The present application is a continuation-in-part of U.S. patent application Ser. No. 14/703,486 filed May 4, 2015, now U.S. Pat. No. 9,345,885, which is a continuation-in-part of U.S. patent application Ser. No. 13/708,129 filed Dec. 7, 2012, now U.S. Pat. No. 9,026,204, which claims priority to U.S. Provisional Patent Application No. 61/567,664 filed Dec. 7, 2011 and U.S. Provisional Patent Application No. 61/567,666 filed Dec. 7, 2011, the disclosures of which are incorporated by reference herein in their entirety.

U.S. patent application Ser. No. 13/708,129 is also related to U.S. patent application Ser. No. 13/708,111 filed on Dec. 7, 2012, now U.S. Pat. No. 9,050,462, and U.S. patent application Ser. No. 13/708,146 filed on Dec. 7, 2012, now U.S. Pat. No. 8,731,683, the disclosures of which are incorporated by reference herein in their entirety.

TECHNICAL FIELD

The present invention relates to the treatment of unilateral vocal cord autoparalysis, and in particular, to devices and methods for stimulating a dysfunctional muscle or stimulating the recurrent laryngeal nerve (RLN) and/or the glottic closure reflex of a human subject to treat the autoparalysis.

BACKGROUND ART

Voicing occurs when air is expelled from the lungs through the glottis, creating a pressure drop across the larynx. When this drop becomes sufficiently large, the vocal folds start to oscillate. The minimum pressure drop required to achieve phonation is called the phonation threshold pressure, and for humans with normal vocal folds, it is approximately 2-3 cm $H_2O$. The motion of the vocal folds during oscillation is mostly laterally, though there is also some superior component as well. However, there is almost no motion along the length of the vocal folds. The oscillation of the vocal folds serves to modulate the pressure and flow of the air through the larynx, and this modulated airflow is the main component of the sound of most voiced phones.

The vocal folds will not oscillate if they are not sufficiently close to one another, are not under sufficient tension or under too much tension, or if the pressure drop across the larynx is not sufficiently large. In linguistics, a phone is called voiceless if there is no phonation during its occurrence. In speech, voiceless phones are associated with vocal folds that are elongated, highly tensed, and placed laterally (abducted) when compared to vocal folds during phonation.

Fundamental frequency, the main acoustic cue for the percept pitch, can be varied through a variety of means. Large scale changes are accomplished by increasing the tension in the vocal folds through contraction of the cricothyroid muscle. Smaller changes in tension can be effected by contraction of the thyroarytenoid muscle or changes in the relative position of the thyroid and cricoid cartilages, as may occur when the larynx is lowered or raised, either volitionally or through movement of the tongue to which the larynx is attached via the hyoid bone. In addition to tension changes, fundamental frequency is also affected by the pressure drop across the larynx, which is mostly affected by the pressure in the lungs, and will also vary with the distance between the vocal folds. Variation in fundamental frequency is used linguistically to produce intonation and tone.

The voicing mechanism that is specifically designed for voice production is the larynx. The larynx is between the pharynx and the trachea. It communicates with the mouth and the nose though the laryngeal and oral parts of the pharynx. Although the larynx is part of the air passages, the larynx normally acts as a valve for preventing swallowed food and foreign bodies from entering the lower respiratory passages. The larynx is located in the anterior portion of the neck.

The laryngeal skeleton comprises nine cartilages that are joined by various ligaments and membranes. Three of the cartilages are single (thyroid, cricoid and epiglottis), and three are paired (arytenoid, corniculate, and cuneiform).

The extrinsic muscles of the larynx move the larynx as a whole. The infrahyoid muscles (omohyoid, sternohyoid, and sternothyroid) are depressors of the hyoid bone and the larynx, whereas the suprahyoid muscles (stylohyoid, digastric, mylohyoid and geniohyoid) and the stylopharyngeus are elevators of the hyoid bone and larynx.

The intrinsic muscles of the larynx are concerned with the movements of the laryngeal parts, making alterations in the length and tension of the vocal folds and in the size and shape of the rima glottidis in voice production. All intrinsic muscles of the larynx are supplied by the recurrent laryngeal nerve (RLN), a branch of the vagus nerve (CN X) except the cricothyroid muscle, which is supplied by the external laryngeal nerve.

The adductors of the vocal folds include the lateral cricoarytenoid muscles which arise from the lateral portions of the cricoid cartilage and insert into the muscular processes or the arytenoid cartilages. These muscles pull the muscular processes anteriorly, rotating the arytenoid cartilages so that their vocal processes swing medially. These movements adduct the vocal folds and close the rima glottidis.

The principle abductors of the vocal folds are the posterior cricoarytenoid muscles. These muscles arise on each side from the posterior surface of the lamina of the cricoid cartilage and pass laterally and superiorly to insert into the muscular processes of the arytenoid cartilages. They rotate the arytenoid cartilages, thereby deviating them laterally and widening the rima glottidis.

The main tensors of the vocal folds are the triangular cricothyroid muscles. These are located on the external surface of the larynx between the cricoid and thyroid cartilages. The muscle on each side arises from the anterolateral part of the cricoid cartilage and inserts into the inferior margin and anterior aspect of the inferior horn of the thyroid cartilage. These muscles tilt the thyroid cartilage anteriorly on the cricoid cartilage, increasing the distance between the thyroid and arytenoid cartilages. As a result, the vocal ligaments are elongated and tightened and the pitch of the voice is raised.

The principle relaxers of the vocal folds are the broad thyroarytenoid muscles. They arise from the posterior surface of the thyroid cartilage near the median plane and insert into the anterolateral surfaces of the arytenoid cartilages. One band of its inferior deep fibers, called the vocalis muscle, arises from the vocal ligament and passes to the vocal process of the arytenoid cartilages anteriorly. The thyroarytenoid muscles pull the arytenoid cartilages anteriorly, thereby slackening the vocal ligaments. The vocalis muscles produce minute adjustments of the vocal ligaments (e.g., as occurs during whispering). They also relax parts of the vocal folds during phonation and singing.

The laryngeal nerves are derived from the vagus nerve (CN X) through the superior laryngeal nerve and the RLN. All intrinsic muscles, except cricothyroid, are innervated by the RLN with fibers from the accessory nerve (CN XI). The external laryngeal nerve supplies the cricothyroid muscle. The supraglottic portion of the laryngeal mucosa is supplied by the internal laryngeal nerve, a branch of the superior laryngeal nerve. The infraglottic portion of the laryngeal mucosa is supplied by the RLN.

Trauma to the RLN causes severe dyspnea because of the paramedian position assumed by bilateral paralyzed vocal cords and the resultant loss of inspiratory abduction and an impaired voice in cases of unilateral damage of vocal cords or innervating nerves because of reduced ability to bring the vocal fold on the damaged side to the midline. Although regeneration of nerve fibers innervating the laryngeal muscles occurs in a large proportion of the damages, the reinnervated vocal cord is not capable of abduction and, therefore, continues to act as an obstruction in the airway. Neither is it capable of adduction and, therefore, the patient suffers from reduced ability to bring the vocal fold on the damaged side to the midline, to create episodes of airway constriction for pitch generation for sound production. Reduced ability to bring the vocal fold on the damaged side to the midline limits the natural behavior of protecting against aspiration during swallowing and valsalva maneuvers essential for building up abdominal tension, e.g., for lifting objects, coughing, micturation and defecation.

SUMMARY OF EMBODIMENTS

In accordance with one embodiment of the invention, a method for treating a human subject having unilateral vocal cord paralysis includes sensing electrical activity of a dysfunctional muscle of the subject, generating at least one stimulation parameter, using a processor, based on the sensed electrical activity, and stimulating the dysfunctional muscle, using a stimulating electrode, based on the at least one stimulation parameter.

In related embodiments, the dysfunctional muscle may be a synkinetically reinnervated muscle. The method may further include providing the stimulating electrode configured to contact the dysfunctional muscle. The stimulating electrode may be configured to sense the electrical activity of the dysfunctional muscle. The stimulating electrode may be configured to be distal to an insertion point of a recurrent laryngeal nerve or vagus nerve into innervated muscle. Stimulating the dysfunctional muscle may stimulate a vocalizing muscle that opens or closes a vocal fold. The vocalizing muscle may include thyroarytenoid muscles, vocalis muscles, posterior cricoarytenoid muscle, lateral cricoarytenoid muscles, and/or cricothyroid muscle. Sensing may include detecting electromyographic (EMG) activity of a vocalizing muscle and/or detecting movement related to voice production. The method may further include determining when the sensed electrical activity has reached a predetermined level, and generating the at least one stimulation parameter when the predetermined level is reached. The method may further include stimulating a recurrent laryngeal nerve or vagus nerve and/or activating a glottic closure reflex based on the at least one stimulation parameter. Activating may include electrical stimulation and/or mechanical stimulation. The stimulation parameters may include a stimulation voltage that is above a threshold for activation of vocal cord adductor muscles of the subject and below a threshold for activation of vocal cord abductor muscles of the subject.

In accordance with another embodiment of the invention, a stimulation system for a human subject having unilateral vocal cord paralysis includes a sensing electrode configured to sense electrical activity of a dysfunctional muscle of the subject, a processor configured to receive the sensed electrical activity of the dysfunctional muscle and configured to generate at least one stimulation parameter based on the sensed electrical activity, and a stimulating electrode configured to stimulate the dysfunctional muscle of the subject based on the at least one stimulation parameter.

In related embodiments, the processor may be configured to detect when the sensed electrical activity has reached a predetermined level and configured to generate the at least one stimulation parameter when the predetermined level is reached. The system may further include a manual activator configured to cause the processor to generate the at least one stimulation parameter. The sensing electrode and the stimulating electrode may be on the same electrode lead. The at least one stimulation parameter may include a stimulation voltage that is above a threshold for activation of vocal cord adductor muscles of the subject and below a threshold for activation of vocal cord abductor muscles of the subject. The sensing electrode may be configured to sense electrical activity of a synkinetically reinnervated dysfunctional muscle.

In accordance with another embodiment of the invention, a method for treating a human subject having unilateral vocal cord paralysis includes providing a sensing electrode configured to detect voice activity of the subject and to generate a first signal and generating at least one stimulation parameter, using a processor, in response to receiving the first signal. The stimulation parameter is based on the first signal. The method further includes activating a glottic closure reflex in response to receiving the stimulation parameter.

In related embodiments, the activating may include electrical stimulation and/or mechanical stimulation. The sensing electrode may be configured to detect electromyographic (EMG) activity of a vocalizing muscle and/or to detect movement related to voice production. The sensing electrode may be a microphone that detects acoustic signals related to voice production, may be an impedance sensor that detects changes of impedances related to voice production, and/or may be a pressure sensor that detects changes in pressure related to voice production. The activating may include providing a current pulse having a duration of about 0.01 msec to 20 msec and a magnitude in the range of about 0.05 mA to 20 mA. The stimulation parameter may include a stimulation frequency that is approximately reciprocal to a contraction time of a vocal cord adductor of the subject and may include a stimulation frequency that is above a reciprocal of a contraction time of a vocal cord abductor of the subject. The stimulation parameter may include a stimulation voltage that is above a threshold for activation of vocal cord abductor or adductor muscles of the subject. Alternatively, the stimulation parameter may include a stimulation voltage that is above a threshold for activation of vocal cord adductor muscles of the subject and below a threshold for activation of vocal cord abductor muscles of the subject. The stimulation parameter may include a stimulation voltage that is above a threshold for activation of vocal cord abductor muscles of the subject and above a threshold for activation of vocal cord adductor muscles of the subject. The stimulation parameter may include a stimulation voltage so that a net force for activation of adductor muscles is higher than a net force for activation of abductor muscles of the subject. The method may further include determining when the voice activity has reached a predetermined level, and then having the sensing electrode generate the first signal when the predetermined level is reached.

In accordance with another embodiment of the invention, a stimulation system for a human subject having unilateral vocal cord autoparalysis includes a manual activator configured to generate a first signal, a processor configured to receive the first signal and to generate at least one stimulation parameter based on the first signal, and a stimulating electrode configured to receive the stimulation parameter from the processor and to activate a glottic closure reflex of the subject based on the stimulation parameter.

In related embodiments, the manual activator may be a switch operable by the subject. The processor may be configured to receive the first signal by inductive coupling, capacitive coupling, electromagnetic transmission, light coupling, vibratory coupling, mechanical coupling and/or acoustical coupling.

In accordance with another embodiment of the invention, a pacemaker system for a human subject having unilateral vocal cord autoparalysis includes a sensing electrode configured to detect voice activity of the subject and to generate a first signal and a processor in communication with the sensing electrode. The processor has program code for receiving the first signal and for generating at least one stimulation parameter based on the first signal in order to activate a glottic closure reflex of the subject. The system further includes a stimulating electrode configured to receive the stimulation parameter and to activate the glottic closure reflex of the subject based on the stimulation parameter.

In related embodiments, the stimulating electrode may be a nerve cuff electrode and/or a rod electrode. The stimulation electrode may be configured to provide a range of stimulation voltages. The processor may be configured to detect when the first signal has reached a predetermined level and may be configured to generate the stimulation parameter when the predetermined level is reached.

In accordance with a further related embodiment, the processor may detect when the first signal has reached a predetermined level and respond by generating the stimulation parameter. Additionally, the processor may include a pulse generator. In accordance with other related embodiments, the electrodes may be bipolar or tripolar. The second signal may be a biphasic current pulse which may have a duration of about 0.001 ms to 50 ms, in most subjects from 0.1 msec to 5 msec, and a magnitude in the range of about 0.05 mA to 20 mA, in most subjects from 0.5 mA to 5 mA.

In accordance with related embodiments, the method may further include providing an energy coupling circuit that inductively couples energy through the skin of the subject. The method may include providing an energy coupling circuit that optically couples energy through the skin of the subject. Stimulating the vocalizing nerve of the subject with an electrical signal may include stimulating the nerve with an electrical signal at a frequency that is approximately reciprocal to the contraction time of the vocal cord adductor of the subject. Stimulating the vocalizing nerve of the subject with an electrical signal may include stimulating the nerve with an electrical signal at a frequency that is above the reciprocal of the contraction time of the vocal cord abductor of the subject.

BRIEF DESCRIPTION OF THE DRAWINGS

The foregoing features of the invention will be more readily understood by reference to the following detailed description, taken with reference to the accompanying drawings, in which:

FIG. 3 is an illustration of a stimulation system for unilateral vocal cord autoparalysis, in accordance with an embodiment of the invention, and FIG. 3A is an exploded view of the circled region in FIG. 3;

DESCRIPTION OF ILLUSTRATIVE EMBODIMENTS

Figure 1:
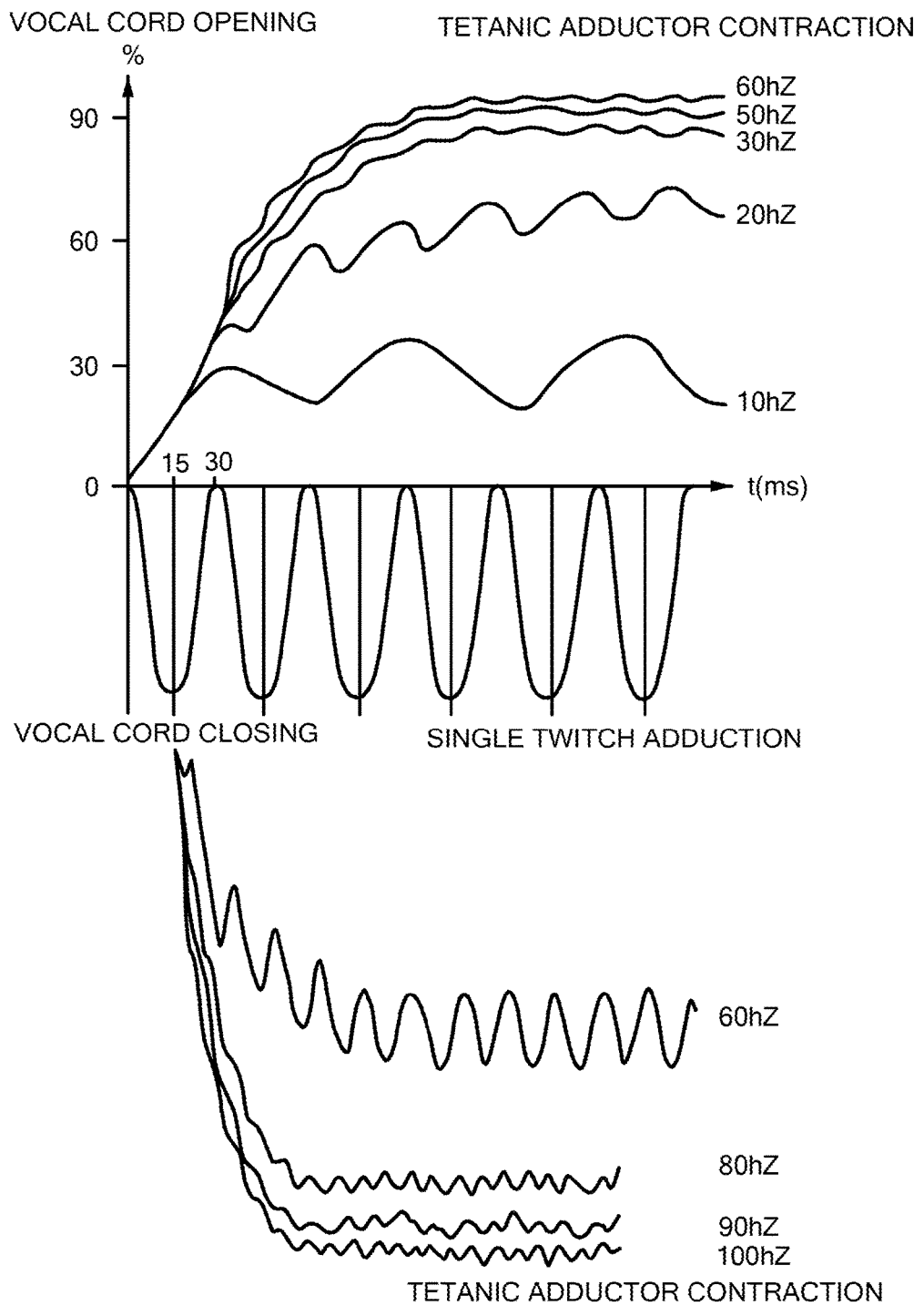
FIG. 1 is a graphical illustration of the underlying principle of frequency-dependent movement of the vocal cords in accordance with an embodiment of the present invention.

There are large differences between bilateral and unilateral vocal fold paralysis, see, e.g., US Patent Publication No. 2002/156507, incorporated by reference herein in its entirety. In bilateral vocal fold paralysis, both vocal folds are paralyzed or autoparalyzed. The impairment is due to the paramedian (almost closed position) of both vocal folds. Therefore, the airway passage is almost closed and the patient has very limited ability to breathe. Because of the position of both vocal folds, however, their voice is almost normal during vocalization.

In unilateral vocal fold paralysis, one vocal fold is paralyzed or autoparalyzed only, and the other one is normally functioning. The impairment is due to the fact that the non-functioning vocal fold cannot be totally closed/medialized. Therefore, even by total medialization of the healthy vocal fold, the gap between the vocal folds cannot be totally closed/medialized, which leads to a breathy or even worse quality of the voice, an increased risk of aspiration, and a reduced ability for valsalva maneuver (a building up of abdominal pressure by expiration against closed vocal folds). Because the healthy vocal fold is able to open normally, patients have no problems with inspiration, at least during normal daily activities. However, during maximum exercise or sports activities, the non-functioning vocal fold is limiting the maximum amount of inspired air, similar to the problem seen in racing and sports horses with laryngeal hemiplegia (recurrent laryngeal neuropathy), see, e.g., US Patent Publication No. 2008/208280 by Lindenthaler et al., incorporated herein by reference in its entirety.

There may be several reasons why one vocal fold is impaired. For example, a reinnervated vocal cord may not be capable of abduction or adduction because the innervation is misdirected (a condition known as synkinetic innervation). Synkinetic innervation occurs when abductor fibers reach and reinnervate the adductor muscles and/or adductor fibers reach and reinnervate the abductor muscles. Consequently, contraction of the adductor muscles occurs during inspiration also, so that any inspiratory contraction of the re-innervated posticus muscle is nullified as an abductor force and total closure of vocal folds is counterbalanced by the antagonistic abductory force of the abducter muscle which co-contracts dissynergetically during voice production, swallowing, coughing, valsalva maneuvers, etc. (a condition known as autoparalysis). Since the abductory and adductory fibers are randomly grouped within the trunk of the RLN, there is no known way of preventing misdirected regeneration of nerve fibers.

Alternatively, the reinnervated vocal cord may not be capable of abduction and/or adduction because of a reduction in the number of re-innervated motor units, (sometimes associated with trophic changes of muscle fibers), disturbance of nerve conductivity, or less maturation of neuromuscular junctions.

In patients suffering from unilateral vocal cord autoparalysis, it was thought that the paralysis was due to the nerve(s) inability to carry action potentials to the muscle to contract the muscle appropriately. Therefore, stimulation of the nerve trunk in patients with this disease was not considered a viable option. However, in synkinetically reinnervated muscle tissue, the muscle is functional and fully stimulated by the nerve(s), but because of dis-synergic co-activation of the synkinetically reinnervated antagonist muscle also (e.g., the timing of activation of agonist and antagonist muscles is incorrect), the functional outcome is a non-sufficient movement. Embodiments of the present invention recognized the benefit of treating unilateral vocal cord autoparalysis by stimulating the RLN or vagus nerve or by activating the glottic closure reflex by electrical and/or mechanical stimulation in order to selectively activate the abductor muscle, the adductor muscles or both. The advantages of nerve stimulation or reflex activation over intramuscular stimulation are less interference of the stimulation electrode from movement of the muscle, the placement of the implanted electrode is distant from the risky, delicate location of nerve muscle endplates, less invasive surgery is required for implanting the stimulation electrode, etc. Alternatively, embodiments of the present invention may include stimulating dysfunctional muscle by electrical stimulation in order to selectively activate the abductor muscle, the adductor muscles or both.

The benefits of using embodiments of the present invention allow the opening and closing of the vocal folds to be activated by the same stimulation electrode based on the stimulation parameters selected due to the differences between the abductor (the opener) and the adductor (the closer) muscles (e.g., frequency-dependent, different thresholds or difference of net forces of adductor and abductor muscles). Exploiting these differences allows for a stimulation system that provides for the selective activation of vocal fold closing muscles, without activation of vocal fold opening muscles, the selective activation of vocal fold opening muscles, without activation of vocal fold closing muscles, and/or the tensioning of vocal folds by graded balanced activation of both opening and closing muscles.

Embodiments of the present invention are directed to a system and method of sensing the vocal activity of a vocalizing muscle contraction in the larynx and/or pharynx and stimulation of the RLN or vagus nerve innervating a vocalizing muscle, e.g., without the electrical stimulation of the muscle fibers directly, based on the sensed activity. Other embodiments of the present invention are directed to a system and method of sensing the vocal activity of a vocalizing muscle contraction in the larynx and/or pharynx and stimulation of the dysfunctional muscle directly based on the sensed activity. In patients suffering from unilateral vocal cord paralysis, the sensed vocalizing muscle is typically a synkinetically reinnervated dysfunctional muscle. Sensing a signal (e.g., electromyographic (EMG) signal) from a dysfunctional muscle, such as a synkinetically reinnervated muscle (e.g., cricoarytenoid muscle) is not typically done. This may be because synkinetically reinnervated muscles, due to their observed behavior, have been considered as being paralyzed and therefore unable to transmit nerve signals at all. However, synkinetically reinnervated muscles, in fact, receive and transmit nerve signal information, but the muscles are just unable to perform like healthy muscles. There are also difficulties with sensing a synkinetically reinnervated muscle because the synkinetically reinnervated muscle returns two EMG signals rather than just one. For example, synkinetically reinnervated cricoarytenoid muscle returns one EMG signal originating from the adductor nerve fibers and another EMG signal from the abductor nerve fibers. Therefore, because the muscle is synkinetically reinnervated, an unpredictable mixture of EMG signals from both adductor and abductor muscles are measured and filtering algorithms should be used in order to extract a usable signal that may be used as a trigger signal for vocal cord pacing. This would allow the surgeon to choose the optimum accessibility to the nerve and/or the dysfunctional muscle.

U.S. Pat. No. 5,111,814 by Goldfarb, incorporated herein by reference, teaches sensing of electrical activity of normally functioning muscle tissue and stimulating of reinnervated muscle tissue of the larynx. In contrast, embodiments of the present invention sense or measure the electrical activity of the dysfunctional muscle tissue, which allows the healthy, normally functioning muscle tissue to remain untouched, minimizing the danger of injuring the healthy muscle tissue. Embodiments may then stimulate the RLN or vagus nerve innervating the dysfunctional vocalizing muscle or stimulate the dysfunctional vocalizing muscle directly.

Embodiments of the present invention are also directed to a system and method of sensing the vocal activity of a vocalizing muscle contraction in the larynx and/or pharynx and activating the glottic closure reflex. This reflex may be activated by stimulation of a nerve, such as the superior laryngeal nerve, the internal or external superior nerve, and/or the glossopharyngeal nerve. It may also be elicited by stimulating mechanoreceptors and/or mucosa of the larynx and/or pharynx, or by the slap reflex. Stimulation may occur by electric currents and/or by mechanical movement or vibration. This variety of stimulation sites may allow a surgeon to choose the optimum treatment for the patient. The glottic closure reflex, in turn, activates the natural fiber tissue which innervates the vocalizing muscles that control the closure of the vocal folds. In some embodiments, stimulation of the RLN or vagus nerve and activation of the glottic closure reflex may be done at the same time. Similarly, in some embodiments, stimulation of the RLN or vagus nerve and/or activation of the glottic closure reflex may be done at the same time as stimulation of the dysfunctional muscle tissue directly.

In some embodiments, the glottis is closed by active electrical sensing/stimulation or electrical sensing and electrical/mechanical stimulation in order to increase the quality of the voice. In contrast, U.S. Pat. No. 5,111,814 is employed to stimulate muscles which open the glottis in order to increase the amount of inspired air. Similarly, US Patent Publication No. 2006/282127 by Zealear, incorporated herein by reference, is employed to open the vocal folds for the same reason. Thus, embodiments of the present method and device are directed to the sensing activity of vocalizing muscle contraction and not respiratory muscle contraction as, e.g., in US Patent Publication No. 2006/282127 by Zealear.

In some embodiments, a manual activator may be used instead of the active sensing of a vocalizing muscle contraction or a dysfunctional vocalizing muscle contraction. The manual activator then activates the RLN, the vagus nerve, the glottic closure reflex, and/or the dysfunctional muscle tissue, e.g., by causing stimulation parameters to be sent to the appropriate locations via the stimulation electrode(s). The manual activator allows the stimulation system to be inactive during periods in which vocalization would not be needed, e.g., during sleep or while eating, but allows it to be manually activated when vocalization is desired.

After active sensing of the vocalizing muscle contraction or manual activation, various stimulation parameters may be used in order to take advantage of the differences between the abductor (the opener) and the adductor (the closer) muscles in terms of the threshold voltage for activation, the contraction time, and the number of fibers. Thus, the stimulation parameters include varying amplitude, frequency and/or threshold. For example, the applied voltage and the stimulation frequency may be chosen such that the desired muscles are activated, either directly and/or via the RLN, the vagus nerve or the glottic closure reflex. In general, the stimulation voltage should be directly proportional to the threshold values and the stimulation frequency indirectly proportional to the contraction times.

Embodiments of the present invention may use the frequency-dependent movement of the vocal cords, as shown in FIG. 1. Such movement occurs as a result of the difference in contraction times between the abductor and adductor muscles. The contraction time of the only existing abductor of the vocal cords, the posterior cricoarytenoid (PCA) muscle, is significantly longer than that of the adductor muscles. The RLN contains the nerve fibers to all muscles that act on the vocal cords (except the cricothyroid (CT) muscle which is innervated by the superior laryngeal nerve (SLN)), randomly distributed over the whole nerve. Consequently, an action potential generated by an electrical stimulation always reaches both abductor and adductor muscles. Thus, the glottis first closes due to the faster adductors, then it opens, and ends with relaxation which leads to a vibration of the vocal cords.

When stimulated at a frequency approximately reciprocal to the contraction time of the vocal cord abductor, the action potentials arrive at the muscles at a time when the adductor muscles will have just relaxed from the last activation when the next pulse arrives (as shown below the zero-line on the graph). The abductor, in contrast, has just reached its maximal contraction when the incoming initiation for the next contraction causes their temporal summation (shown above the zero-line). Consequently, resulting tetanic abductor tension overcomes the weaker single twitch adduction.

For stimulation at a frequency approximately reciprocal to the contraction time of the vocal cord adductor, the adductor muscles also reach tetanic contraction, and due to their greater number (4:1) the vocal cords are closed.

Embodiments of the present invention may use the different thresholds for electrical activation for the nerves innervating the abductor and adductor muscles. The threshold for activation for abduction is higher than the threshold for adduction because the contraction time of the PCA muscle is significantly longer than that of the adductor muscles. Therefore, the PCA muscle is innervated by nerve fibers of smaller mean nerve fiber diameter which have a threshold for electrical activation higher than for nerve fibers of higher mean nerve fiber diameter, such as innervating the adductor muscles.

When stimulated by a stimulation voltage above the threshold for activation of the nerve fibers innervating the adductor muscle but below the threshold for activation of the nerve fibers innervating the abductor muscle, the abductor muscle fibers will not be activated and therefore relaxed. In contrast, nerve fibers innervating the adductor muscle fibers will be activated, leading to a contraction of the adductor muscles, and the vocal cords will close. When the stimulation voltage is above the respective thresholds for activation for both abductor and adductor muscles, then both sets of muscles will be stimulated. The larger the stimulation amplitude (i.e., the injected amount of charge), the stronger both the abductor and adductor muscles are activated independent of the chosen stimulation frequency, provided the stimulation voltage is above each respective threshold.

Embodiments of the present invention may use the difference of net forces of adductor and abductor muscles due to electrical activation for the nerves innervating the abductor and adductor muscles. The net force for activation of adductor muscles is higher than the net force for activation of abductor muscles due to their greater number (4 adductor muscles versus 1 abductor muscle per side).

When stimulated by a stimulation voltage above the threshold for activation of the nerve fibers innervating the adductor muscles and above the threshold for activation of the nerve fibers innervating the abductor muscle, the abductory (vocal fold opening) net force of the abductor muscle fibers will be lower than the adductory (vocal fold closing) net force of the adductor muscle fibers, as a sum of forces leading to a closing of the vocal folds.

Thus, the stimulation parameters should be selected based on the desired application and selective activation. In summary, when the stimulation voltage is below the threshold value for activation of the adductors, then no stimulation occurs regardless of the stimulation frequency or amplitude used. When the stimulation voltage is above the threshold value for activation of the adductors, but below the threshold value for activation of the abductors, then the vocal folds are closed, regardless of the stimulation frequency or amplitude used, which should benefit patients having unilateral vocal cord autoparalysis. When the stimulation voltage is above the threshold value for activation of the abductors (and thus above the threshold value for activation of the adductors as well), then the vocal folds may be opened due to tetanic contraction of the abductor muscle when the stimulation frequency is approximately the stimulation frequency of the abductor muscle and the amplitude is low. However, the vocal folds may be opening when these same conditions are applied (the stimulation voltage is above the threshold value for activation of the abductors and the stimulation frequency is approximately the stimulation frequency of the abductor muscle) but a high amplitude is used such that the force of tetanically contracted abductor muscle is greater than the twitch contractions of the adductor muscles. If an even higher amplitude is used such that the force of tetanically contracted abductor muscle is less than the twitch contractions of the adductor muscles, then the vocal folds may be closing (although there may be a ripple or vibration depending on the stimulation frequency) because the high applied amplitude overrules tetanic contraction of the abductor muscle. When the stimulation voltage is above the threshold value for activation of the abductors and the stimulation frequency is approximately the stimulation frequency of the adductor muscle, then the vocal folds are closed, regardless of the amplitude used, which should benefit patients having unilateral vocal cord autoparalysis. For example, depending on the stimulation parameters, a low amplitude may be less than approximately 1.5 mA, a high amplitude may be about 1 to 3 mA, and a very high amplitude may be greater than about 2.5 mA, for a pulse duration of about 0.5 ms.

Consequently, based on the stimulation parameters used (such as described above, as well as other combinations), there may be various switching scenarios for the adductor and abductor muscles that are beneficial to selectively activate the vocalizing muscles. For example, with the selection of a stimulation frequency approximately equal to the stimulation frequency of the abductor muscle, a low amplitude, and a stimulation voltage greater than the stimulation voltage for the adductor muscles, the stimulation voltage may be switched between a voltage less than the stimulation voltage of the abductor muscle to a stimulation voltage greater than the stimulation voltage of the abductor muscle, which causes the vocal cords to switch between a closed and an open state. Similarly, with the selection of a stimulation frequency approximately equal to the stimulation frequency of the abductor muscle and the stimulation voltage to greater than the stimulation voltage for the abductor muscles, the amplitude may be switched between a low value and a high value (or very high value), which causes the vocal cords to switch between an opened and an opening (or closing) state. Likewise, with the selection of a stimulation frequency approximately equal to the stimulation frequency of the abductor muscle and a low amplitude, the stimulation frequency may be switched between the stimulation frequency of the abductor muscle and the adductor muscles, which causes the vocal cords to switch between an opened and a closed state.

Embodiments of the present invention include stimulation electrode(s) that are configured to provide various stimulation voltages, frequencies and/or amplitudes, so that the various stimulation parameters may be implemented.

In some embodiments of the present invention, the synkinetically re-innervated nerve, and not the muscle directly, is stimulated because more than 10 times less power is necessary for activation of a nerve than of the muscle itself. Additionally, a nerve-cuff-electrode can be positioned along the nerve far from moving muscles and tissue and far from sensitive receptors, which would produce unwanted reactions. In some embodiments, the synkinetically reinnervated muscle is stimulated directly with parameters that are needed for the activation of the muscle, as known by one skilled in the art. For example, Sanders describes stimulation parameters for laryngeal muscles in "Electrical Stimulation of Laryngeal Muscle," *Otolaryngologic Clinics of North America*, Vol. 24, No. 5, October 1991, pages 1253-1274, which is incorporated by reference herein in its entirety.

Figure 2:
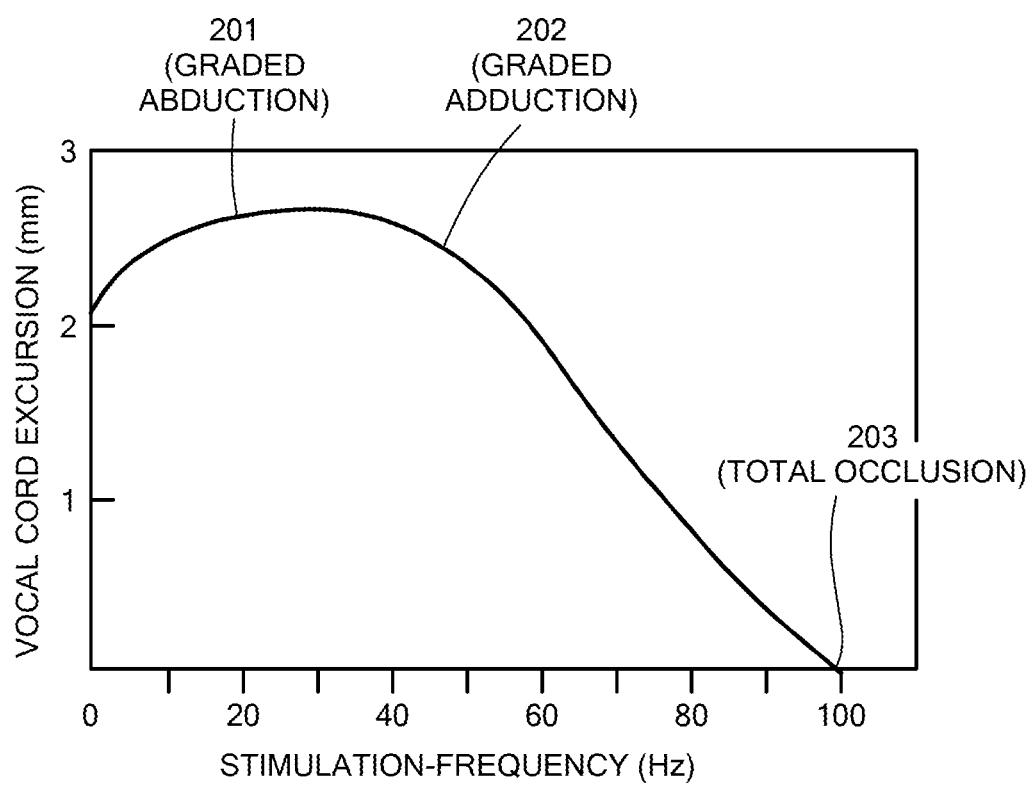
FIG. 2 is a graphical illustration of the frequency-dependent motion of the vocal cords in accordance with the embodiment of FIG. 1.

FIG. 2 is a graphical illustration of the frequency-dependent motion of the vocal cords. Stimulation at 10 to 30 Hz causes a graded abduction 201 of the vocal cords. Above 30 Hz graded cord adduction occurs 202, with total airway occlusion 203 at 100 Hz by bilateral stimulation.

FIGS. 3 and 3A are illustrations of a stimulation system according to one embodiment of the present invention. A stimulation system for unilateral vocal cord paralysis includes one or more stimulating (efferent) electrodes 301 and optionally may include one or more sensing (afferent) electrodes (not visible) or a manual activator that may be activated by the user, e.g., a switch or toggle, instead of, or in addition to, the sensing electrodes. Alternatively, the one or more stimulating electrodes 301 may be used as both the sensing and stimulating electrode(s). The stimulation system also includes a processor 303, which may include a pulse generator. The processor 303 may be implanted in the patient's chest, and the stimulating electrodes 301 may be wrapped around or placed near or in contact with the vagus nerve or RLN 302 along with the electrode leads 304 and safety loops 305 or may be placed near or in contact with the dysfunctional muscle tissue directly (not shown). For example, one or more stimulating electrodes 301 may be provided at an insertion point of the vocalizing nerve into an innervated muscle, such as a synkinetically reinnervated dysfunctional muscle. In this way, a single electrode 301, or more than one electrode 301, may be used to sense the electrical activity of the synkinetically reinnervated dysfunctional muscle and to send the sensed electrical activity to the processor 303, which generates at least one stimulation parameter. The single electrode 301 may then receive the stimulation parameters from the processor 303 and stimulate the RLN or vagus nerve or stimulate the dysfunctional muscle tissue directly based on the received stimulation parameters. Alternatively, the stimulation electrodes 301 may be used indirectly to stimulate the RLN or vagus nerve by activating the glottic closure reflex, by stimulation of a nerve, such as the superior laryngeal nerve, the internal or external superior nerve, and/or the glossopharyngeal nerve. The stimulation electrodes 301 may be used to stimulate the glottic closure reflex by stimulating mechanoreceptors and/or mucosa of the larynx and/or pharynx, or by the slap reflex. As mentioned above, the stimulation may be electrical and/or mechanical or vibratory stimulation.

Embodiments of the present system may be totally or partially implanted in a human subject. For example, the stimulator may include a housing that can be very small with all of the implant's electronic components contained in a robust and compact hermetically sealed case. Energy and necessary information may be inductively or optically transferred through the skin of the subject. This can be achieved by either enclosing the electronic circuitry inside a metallic case with a secondary coil placed aside or around the case. Similarly, this may be achieved by enclosing the electronic circuitry and a secondary coil inside a dielectric case.

Figure 4A:
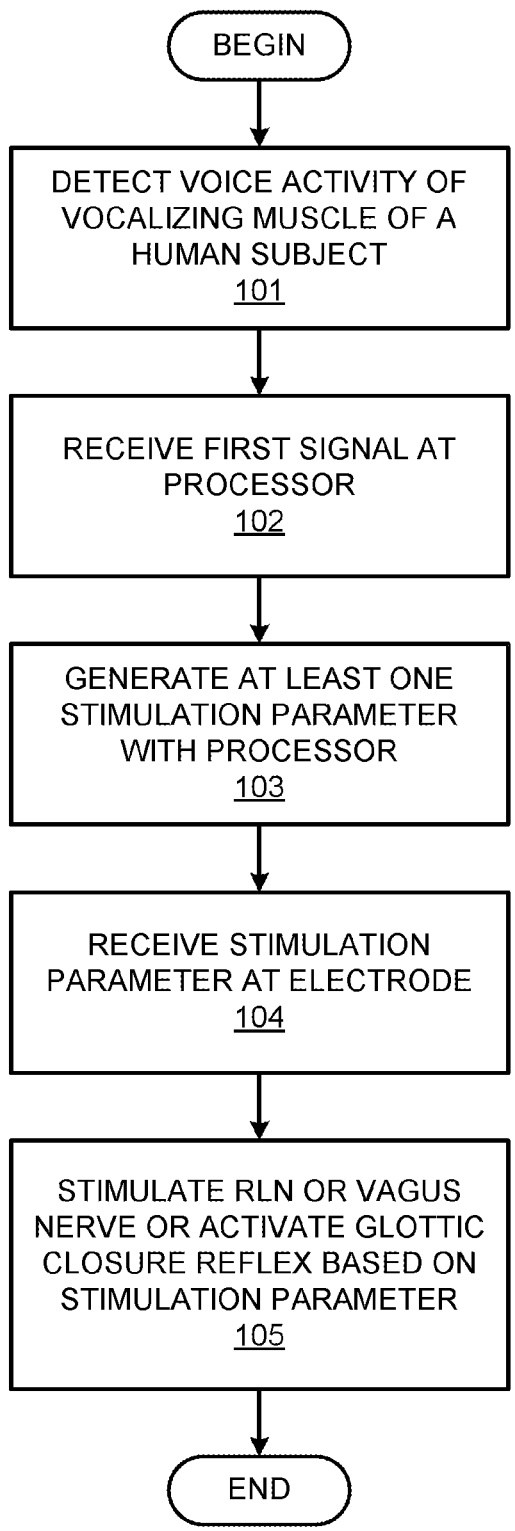
FIG. 4A is a flow chart illustrating a method for stimulating a vocalizing nerve in a human subject having unilateral vocal cord autoparalysis in accordance with an embodiment of the invention.

Referring also to FIG. 4A, the sensing (afferent) part of the closed loop system may include one or more sensing electrodes, or the stimulating electrodes as mentioned above, that detect the voice activities of the infrahyoidal muscles or signals recorded by the alternative sensors (step 101). For example, the sensing electrode(s) or stimulating electrodes (s) may be configured to detect electromyographic (EMG) activity of a vocalizing muscle and/or to detect movement related to voice production. The sensing electrode may be a microphone that detects acoustic signals related to voice production, an impedance sensor that detects changes of impedances related to voice production, and/or a pressure sensor that detects changes in pressure related to voice production. The sensing electrode or stimulating electrode generates a first signal in response to the activity that has been detected.

The first signal is received (step 102) at a processor 303. The processor 303 may include a pulse generator. The processor 303 receives the first signal from the sensing electrode or stimulating electrode and generates at least one stimulation parameter (step 103) that is based on the first signal. The stimulation parameter or second signal may be a biphase current pulse, and the biphase current pulse may have a duration of about 0.001 ms to 50 ms, in most subjects from about 0.1 msec to 5 msec, and a magnitude in the range of about 0.05 mA to 20 mA, in most subjects from about 0.5 mA to 5 mA.

The stimulation parameter from the processor 303 is received by one or more stimulating electrodes 301 (step 104), and the stimulating electrode(s) 301 stimulate a vocalizing nerve, such as the RLN or the vagus nerve directly (from which the RLN originates and which is easier to handle surgically), in accordance with the stimulation parameter. Alternatively, the stimulating electrode(s) 301 may stimulate the RLN or the vagus nerve indirectly by activating the glottic closure reflex(es) (step 105), which then activates the RLN or vagus nerve. In accordance with an embodiment of the invention, the stimulation is limited to the time periods of voice production or swallowing or valsalva maneuver. Outside these activities, the synkinetic reinnervated vocal fold passively relaxes to the paramedian position.

Figure 4B:
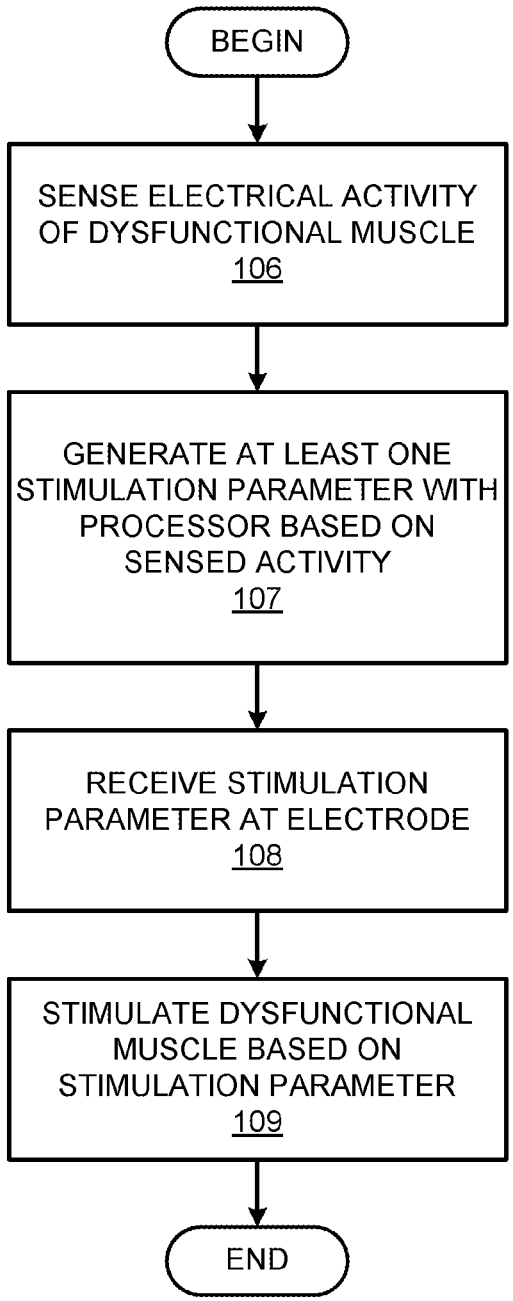
FIG. 4B is a flow chart illustrating a method for stimulating a dysfunctional muscle in a human subject having unilateral vocal cord paralysis in accordance with an embodiment of the invention.

Referring to FIG. 4B, the sensing (afferent) part of the closed loop system may include one or more sensing electrodes, or the stimulating electrodes as mentioned above, that sense the voice activities of the infrahyoidal muscles or signals recorded by the sensors (step 106). For example, the sensing electrode(s) or stimulating electrodes(s) may be configured to detect electromyographic (EMG) activity of a dysfunctional vocalizing muscle, such as a synkinetically reinnervated dysfunctional muscle, and/or to detect movement related to voice production. The sensing electrode or stimulating electrode generates a first signal in response to the activity that has been detected.

The first signal is received at the processor 303, which may include a pulse generator. The processor 303 receives the first signal from the sensing electrode or stimulating electrode and generates at least one stimulation parameter (step 107) that is based on the sensed activity. The stimulation parameter or second signal may be a biphase current pulse and the biphase current pulse may have a duration of about 0.01 ms to 5 ms, in most subjects from about 0.1 ms to 5 ms, and a magnitude in the range of about 0.05 mA to 10 mA, in most subjects from about 0.5 mA to 5 mA. In order to generate a fused contraction, the frequency is preferably above the tetanic frequency of the muscle, e.g., about 30 Hz for the PCA muscle and about 50-70 Hz for the adductor muscles of the larynx. As known by those skilled in the art, the parameters used for stimulating an innervated muscle, such as a synkinetically reinnervated dysfunctional muscle, require about 100 times less energy (i.e., pulse amplitude times pulse duration) than to stimulate denervated muscle. See "Electrical Stimulation of Laryngeal Muscle" by Sanders, *Otolaryngologic Clinics of North America*, Vol. 24, No. 5, October 1991, pages 1253-1274, which is incorporated by reference herein in its entirety, for a discussion of stimulation parameters for laryngeal muscles.

The at least one stimulation parameter from the processor 303 is received by one or more stimulating electrodes 301 (step 108), and the stimulating electrode(s) 301 stimulate a dysfunctional muscle, such as a synkinetically reinnervated dysfunctional muscle, based on the stimulation parameter (step 109). In accordance with an embodiment, the stimulation may be limited to the time periods of voice production or swallowing or valsalva maneuver. Outside these activities, the synkinetic reinnervated vocal fold passively relaxes to the paramedian position.

The stimulating electrodes and the sensing electrodes may be either bipolar or tripolar. Similarly, one electrode may be bipolar and one electrode may be tripolar. The electrode leads 304 should be sufficiently damage-resistant. The lead body should be arranged in a way, so that the nerve and the stimulator are influenced as little as possible by movements of the muscles, the neck and the head.

Embodiments can be used to activate the vocal cord adduction in autoparalysis patients (where the adductor muscles are re-innervated but in a misdirected way) by stimulating the muscle directly, stimulating the whole innervating RLN or alternatively, the vagus nerve, from which the RLN originates. This treatment is effective with respect to autoparalysis patients because it is based on muscle characteristics and not on nerve or muscle/nerve characteristics only.

Figure 5:
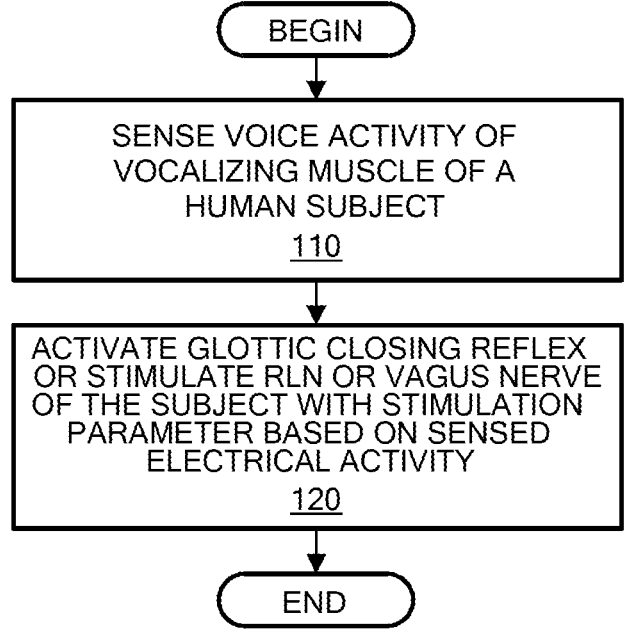
FIG. 5 is a flow chart illustrating a method for pacing laryngeal activity of a human subject in accordance with an embodiment of the invention.

FIG. 5 is a flow chart illustrating a method of pacing laryngeal activity of a human subject in accordance with one embodiment of the invention. Electrical activity of a vocalizing muscle (such as the infrahyoidal muscles) of a human subject is sensed (step 110), and a vocalizing nerve (such as the RLN or the vagus nerve) of the subject is directly stimulated with an electrical signal in synchronism with the sensed electrical activity (step 120). Alternatively, after electrical activity is sensed, the RLN or the vagus nerve may be indirectly stimulated by the activation of the glottic closure reflex(es) (step 120). The stimulation/activation parameters may include stimulating the glottic closure reflex with an electrical signal at a stimulation frequency above the reciprocal value of the contraction time of the vocal cord adductor of the subject. Stimulating the vocalizing nerve of the subject with an electrical signal may include stimulating the nerve with an electrical signal at a frequency approximately reciprocal to the contraction time of the vocal cord adductor of the subject and above the reciprocal of the contraction time of the vocal cord abductor of the subject.

Figure 6:
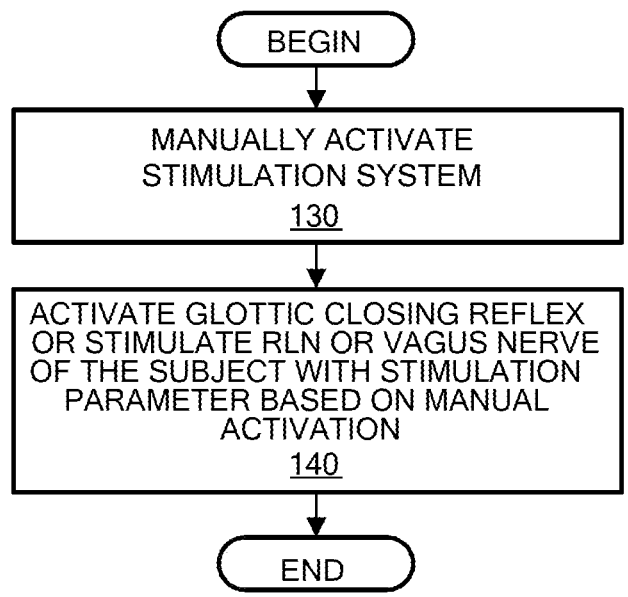
FIG. 6 is a flow chart illustrating a method for pacing laryngeal activity of a human subject using a manual activator in accordance with an embodiment of the invention.

FIG. 6 is a flow chart illustrating a method of pacing laryngeal activity of a human subject using a manual activator in accordance with one embodiment of the invention. The stimulation system is manually activated in step 130. The manual activator may send a first signal to the processor 303, which may include a pulse generator. The processor 303 receives the first signal from the manual activator and generates at least one stimulation parameter that is based on the first signal. A vocalizing nerve (such as the RLN or the vagus nerve) of the subject is directly stimulated with an electrical signal in synchronism with the sensed electrical activity (step 140). Alternatively, or in addition, after electrical activity is sensed, a glottic closure reflex is then activated (step 140) based on the stimulation parameter, which in turn stimulates the RLN or vagus nerve of the subject. The stimulation may be electrical and/or mechanical or vibratory stimulation.

Some embodiments of the processor 303 may be implemented as hardware, software (e.g., a computer program product), or a combination of both software and hardware. For example, embodiments may be implemented as a computer program product for use with a computer system. Such implementation may include a series of computer instructions or program code fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions may embody all or part of the functionality previously described herein with respect to the processor. Those skilled in the art should appreciate that such computer instructions may be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web).

While the invention has been described in connection with specific embodiments thereof, it will be understood that it is capable of further modification. This application is intended to cover any variation, uses, or adaptions of the invention and including such departures from the present disclosure as come within known or customary practice in the art to which the invention pertains.

What is claimed is:

1. A method of treating a human subject having unilateral vocal cord paralysis, the method comprising:
    sensing electrical activity of a dysfunctional muscle of the subject;
    generating at least one stimulation parameter, using a processor, based on the sensed electrical activity; and
    stimulating the dysfunctional muscle, using a stimulating electrode, based on the at least one stimulation parameter.

2. The method of claim 1, wherein the dysfunctional muscle is a synkinetically reinnervated muscle.

3. The method of claim 1, further comprising providing the stimulating electrode configured to contact the dysfunctional muscle.

4. The method of claim 1, wherein the stimulating electrode is configured to sense the electrical activity of the dysfunctional muscle.

5. The method of claim 1, wherein the stimulating electrode is configured to be distal to an insertion point of a recurrent laryngeal nerve or vagus nerve into innervated muscle.

6. The method of claim 1, wherein stimulating the dysfunctional muscle stimulates a vocalizing muscle that opens or closes a vocal fold.

7. The method of claim 6, wherein the vocalizing muscle is selected from the group consisting of thyroarytenoid muscles, vocalis muscles, posterior cricoarytenoid muscle, lateral cricoarytenoid muscles, cricothyroid muscle and combinations thereof.

8. The method of claim 1, wherein sensing includes detecting electromyographic (EMG) activity of a vocalizing muscle, detecting movement related to voice production, or both.

9. The method of claim 1, further comprising:
    determining when the sensed electrical activity has reached a predetermined level; and
    generating the at least one stimulation parameter when the predetermined level is reached.

10. The method of claim 1, further comprising stimulating a recurrent laryngeal nerve or vagus nerve or activating a glottic closure reflex based on the at least one stimulation parameter.

11. The method of claim 10, wherein activating includes electrical stimulation, mechanical stimulation, or a combination thereof.

12. The method of claim 1, wherein the at least one stimulation parameter includes a stimulation voltage that is above a threshold for activation of vocal cord adductor muscles of the subject and below a threshold for activation of vocal cord abductor muscles of the subject.

13. A stimulation system for a human subject having unilateral vocal cord paralysis, the system comprising:
    a sensing electrode configured to sense electrical activity of a dysfunctional muscle of the subject;
    a processor configured to receive the sensed electrical activity of the dysfunctional muscle and configured to generate at least one stimulation parameter based on the sensed electrical activity; and
    a stimulating electrode configured to stimulate the dysfunctional muscle of the subject based on the at least one stimulation parameter.

14. The stimulation system of claim 13, wherein the processor is configured to detect when the sensed electrical activity has reached a predetermined level and configured to generate the at least one stimulation parameter when the predetermined level is reached.

15. The stimulation system of claim 13, further comprising a manual activator configured to cause the processor to generate the at least one stimulation parameter.

16. The stimulation system of claim 13, wherein the sensing electrode and the stimulating electrode are on the same electrode lead.

17. The stimulation system of claim 13, wherein the at least one stimulation parameter includes a stimulation voltage that is above a threshold for activation of vocal cord adductor muscles of the subject and below a threshold for activation of vocal cord abductor muscles of the subject.

18. The stimulation system of claim 13, wherein the sensing electrode is configured to sense electrical activity of a synkinetically reinnervated dysfunctional muscle.

* * * * *